(12) United States Patent
Bettenhausen et al.

(10) Patent No.: US 9,534,245 B2
(45) Date of Patent: Jan. 3, 2017

(54) METHOD AND DEVICE FOR CONTROLLING THE FERMENTATION PROCESS

(75) Inventors: Kurt Dirk Bettenhausen, Bischofsheim (DE); Shun Jie Fan, Beijing (CN); Herbert Grieb, Malsch (DE); Jun Feng Jiang, Beijing (CN); Hongwei Yang, Karlsruhe (DE); Yue Zhuo, Beijing (CN)

(73) Assignee: Siemens Aktiengesellschaft, Munich (DE)

( * ) Notice: Subject to any disclaimer, the term of this patent is extended or adjusted under 35 U.S.C. 154(b) by 1447 days.

(21) Appl. No.: 12/989,375

(22) PCT Filed: Apr. 23, 2008

(86) PCT No.: PCT/CN2008/000830
§ 371 (c)(1),
(2), (4) Date: Nov. 3, 2010

(87) PCT Pub. No.: WO2009/129654
PCT Pub. Date: Oct. 29, 2009

(65) Prior Publication Data
US 2011/0039297 A1    Feb. 17, 2011

(51) Int. Cl.
*C12M 1/36* (2006.01)
*C12Q 1/06* (2006.01)
(Continued)

(52) U.S. Cl.
CPC ............... *C12Q 1/02* (2013.01); *C12M 41/46* (2013.01); *C12M 41/48* (2013.01); *C12M 43/00* (2013.01);
(Continued)

(58) Field of Classification Search
CPC ....... C12M 41/46; C12M 41/48; C12M 43/00; C12Q 1/02; G01N 33/569; G01N 33/5005; G01N 33/56966; G01N 33/56911
(Continued)

(56) References Cited

U.S. PATENT DOCUMENTS 4,856,421 A    8/1989    Whitford
5,629,202 A    5/1997    Chan
(Continued)

FOREIGN PATENT DOCUMENTS

CN          1 778 887         5/2006
DE    10 2004 040 774         4/2006
(Continued)

OTHER PUBLICATIONS

Henson, M.A., "Dynamic modeling and control of yeast cell populations in continuous biochemical reactors", Computers and Chemical Engineering, 2003, 27: 1185-1199.
(Continued)

*Primary Examiner* — Michael Hobbs
*Assistant Examiner* — Liban Hassan
(74) *Attorney, Agent, or Firm* — Cozen O'Connor (57) ABSTRACT

A method and device for controlling a fermenting process, wherein the method comprises collecting samples of biological cells from a fermenting tank, obtaining the state information of the current biological cells based on the collected samples, comparing the state information of the current biological cells with preset target status information to obtain the difference between the state information of the current biological cells and preset target state information, and controlling the feed rate of nutritional solution into the fermenting tank. Real time control of biological fermenting process is thus accomplished based on the state information (Continued)

of the biological cells during fermentation, and the consistency during fermentation is improved. Complicated mathematical modeling and man-made data analysis are not required for the method and device. Real time control of biological fermenting process is accomplished based on a feedback loop with simply calculation, and control delay is not created, and automatic control of cells statement in fermentation is achieved.

5 Claims, 4 Drawing Sheets (51) Int. Cl.
C12Q 1/02 (2006.01)
G01N 33/50 (2006.01)
G01N 33/569 (2006.01)
C12M 1/34 (2006.01)
C12M 1/00 (2006.01)

(52) U.S. Cl.
CPC ........ *G01N 33/5005* (2013.01); *G01N 33/569* (2013.01); *G01N 33/56911* (2013.01); *G01N 33/56966* (2013.01)

(58) Field of Classification Search
USPC .................................. 435/286.5, 39
See application file for complete search history.

(56) References Cited

U.S. PATENT DOCUMENTS

| 5,735,274 | A | 4/1998 | Shibata et al. |
| 6,068,995 | A | 5/2000 | Kobayashi et al. |
| 6,555,360 | B1 | 4/2003 | Srienc et al. |
| 6,861,847 | B2 | 3/2005 | Yamagishi et al. |
| 6,874,355 | B2 | 4/2005 | Kornfeldt et al. |
| 2005/0158701 | A1* | 7/2005 | West ................................ 435/3 |
| 2005/0208473 | A1 | 9/2005 | Krichevsky et al. |
| 2006/0216818 | A1 | 9/2006 | Amano |
| 2007/0236681 | A1* | 10/2007 | Ilkov ............................... 356/73 |
| 2008/0133044 | A1 | 6/2008 | Grieb et al. |
| 2010/0120082 | A1 | 5/2010 | Brahmbhatt |

FOREIGN PATENT DOCUMENTS

| EP | 0661380 A2 | 7/1995 |
| EP | 1728853 A1 | 12/2006 |
| GB | 2 362 000 | 11/2001 |
| JP | 10 260 128 | 9/1998 |
| WO | WO 02083836 A2 | 10/2002 |
| WO | WO 2007/051315 | 5/2007 |

OTHER PUBLICATIONS

Schuügerl, K., "Progress in monitoring, modeling and control of bioprocesses during the last 20 years", Journal of Biotechnology, 2001, 85: 149-173.

Mantzaris, N.V. et al., "Cell population balance modeling and control in continuous bioreactors", Journal of Process Control, 2004, 14: 775-784.

Xiao, jong jie et al., "A-self made lysing solution in flow cytometry on white blood cell sand red blood cells", Journal of Shandong University (Health Sciences), vol. 44, No. 9, 2006 (2 pages).

Rui Zhao et al; "A Flow Injection Flow Cytometry System for On-Line Monitoring of Bioreactors"; Biotechnology and Bioengineering; vol. 62; No. 5; pp. 609-617; ISSN: 0006-3592; DOI: 10.1002/(SICI)1097-0290(19990305)62:5<609::AID-BIT13>3.0. CO; ; XP055071525; 1999; Mar. 5, 1999.

* cited by examiner

METHOD AND DEVICE FOR CONTROLLING THE FERMENTATION PROCESS

CROSS-REFERENCE TO RELATED APPLICATIONS

This is a U.S. national stage of International Application No. PCT/CN2008/000830, filed on 23 Apr. 2008. The entire content of the application is incorporated herein by reference.

BACKGROUND OF THE INVENTION

1. Field of the Invention

The present invention relates to bioengineering technology, and more particularly to a method and device for controlling the fermentation process.

2. Description of the Related Art

The biological fermentation process is a key technique in various industrial fields, such as biopharmaceuticals, biological energy, foods and beverages and environmental protection. An important goal of the biological fermentation process is to improve the consistency of the production process. However, due to the time-dependent change and non-linear properties of the biological fermentation process and the effect of other indeterminable factors, there are often considerable variations among different fermentation batches. How to control the biological fermentation process to deliver high consistency so as to improve the fermentation quality has become an important direction for research.

The biological fermentation process in the present invention includes biological fermentation and cell culture. Industrial biological fermentation processes normally occur in a fermenting tank in which nutrient solution is added and suitable environmental conditions are maintained so that biological cells grow and reproduce in the nutrient solution and produce desired products. The operator or automatic control system can control the biological fermentation process by adjusting the feed rate of the nutrient solution flow to the fermenting tank. In conventional processes open-loop control of the fermentation process is achieved by monitoring and analyzing fermenting environment parameters, such as temperature and pH value of the nutrient solution and concentration of dissolved oxygen, and following a predetermined nutrient solution feeding strategy. However, these control methods only involve external factors such as fermenting environment, but ignore the status changes of biological cells, especially the effect of status changes such as cell size, shape and structure, on the fermentation process. The status changes of biological cells during the fermentation process imposes considerable effects on the fermentation process. Consequently, it is difficult for these conventional control methods to ensure the consistency of the fermentation process.

SUMMARY OF THE INVENTION

It is therefore an object of the present invention is to provide a method and device for controlling a fermentation process to achieve control of the bio-fermentation process based on the status information of the biological cells, thus improving the consistency of the fermentation process.

This and other objects and advantages are achieved in accordance with the invention by providing a method for controlling the fermentation process in which samples of biological cells are collected from a fermenting tank and the current status information of the biological cells are obtained based on the collected biological cell samples, the current status information of the biological cells is compared with preset target status information to obtain a difference status between the current status information of the biological cells and the target status information, and the feed rate of the nutrient solution flow to the fermenting tank is controlled based on the obtained difference status.

In accordance with the invention, obtaining the current status information of the biological cells based on the collected biological cell samples comprises collecting, with a flow cytometer, the biological cell samples from the fermenting tank, and outputting a scatter plot comprising the current status information of the biological cells based on the collected biological cell samples.

Here, the status information comprises at least one cell concentration information, cell size information, cell form information, cell structure information and cell metabolism information.

In accordance with the invention, comparing the current status information of the biological cells with the preset target status information comprises comparing a scatter plot of current status information of the biological cells with the scatter plot of the preset target status information.

In accordance with the invention, obtaining the difference status between the current status information of the biological cells and preset target status information comprises determining a center of gravity of the scatter plot of the current status information of the biological cells and the center of gravity of the scatter plot of the preset target status information, and determining the vector characterizing the difference status, where the vector starts from the center of gravity of the scatter plot of the current status information of the biological cells, and points to and ends at the center of gravity of the scatter plot of the preset target status information.

In accordance with the invention, controlling the feed rate comprises converting the vector characterizing the difference status to a scalar determining the feed rate of nutrient solution flow that minimizes the scalar based on the converted scalar, and feeding the nutrient solution to the fermenting tank at the determined feed rate of nutrient solution flow.

In an alternative embodiment, the step of controlling the feed rate comprises determining the feed rate of nutrient solution flow based on the obtained difference status by using the present flow feed rate determination methodology, and feeding the nutrient solution to the fermenting tank at the determined feed rate of nutrient solution flow, where the flow feed rate determination methodology causes the status information of the biological cells in said fermenting tank to converge to said target status information.

Here, the flow feed rate determination methodology includes proportional-integral-derivative (PID), model predictive control, fuzzy control and neural network control.

Before feeding the nutrient solution flow to the fermenting tank at the determined feed rate of the nutrient solution flow, the method additionally includes judging whether the determined feed rate of nutrient solution flow is within the range of the preset flow feed rate. If the determined feed rate of nutrient solution flow is within the range of the preset flow feed rate, then the nutrient solution flow is fed to the fermenting tank at the determined feed rate of nutrient solution flow. If the determined feed rate of nutrient solution flow is not within the range of the preset flow feed rate, then the nutrient solution flow is fed to the fermenting tank at the preset target feed rate of nutrient solution flow.

After performing the collection of the samples of biological cells from the fermenting tank and obtaining the current status information of the biological cells based on the collected biological cell samples, the method then commences by controlling the feed rate of the nutrient solution flow to the fermenting tank based on the obtained difference status.

In accordance with an object of the invention, a device for controlling the fermentation process comprises a status information acquisition unit, a comparison unit and a control unit.

Here, the status information acquisition unit is used to collect samples of biological cells from the fermenting tank and obtain the current status information of the biological cells according to the biological cell samples.

The comparison unit is used to compare the current status information of the biological cells with preset target status information, obtain a difference status between the current status information of the biological cells and the preset target status information, and provide the difference status to the control unit.

The control unit is used to control the feed rate of nutrient solution flow to the fermenting tank based on the difference status.

Here, the status information acquisition unit is a flow cytometer, comprising a collection subunit, a flow chamber, a laser generator and a detector.

The collection subunit is used to collect samples of biological cells from the fermenting tank and inject the biological cell samples into a center of sheath fluid in a flow chamber which is used to allow the biological cells in the samples to align in a single file and form a cell bundle under restriction of the sheath fluid.

The laser generator is used to generate a laser and excite the cell bundle to produce light information.

The detector is used to obtain the current status information of the biological cells from the light information.

In accordance with the invention, the device further comprises a target status information storage unit for storing the target status information.

Here, the comparison unit is also used to obtain the target status information from the target status information storage unit.

In accordance with the invention, the control unit comprises a flow feed rate determination subunit and a feeding operation subunit where the flow feed rate determination subunit is used to determine the feed rate of nutrient solution flow based on the difference status by using the predetermined flow feed rate determination methodology which causes the status information of the biological cells in the fermenting tank to converge to the target status information, and to send the feed rate of nutrient solution flow to the feeding operation subunit.

The feeding operation subunit is used to feed the nutrient solution to the fermenting tank based on the received feed rate of nutrient solution flow.

In an embodiment, the control unit further comprises a judgment subunit, which is used to receive the feed rate of nutrient solution flow sent from the flow feed rate determination subunit, and to judge whether the feed rate of nutrient solution flow is within the preset flow feed rate range. If the feed rate of nutrient solution flow is within the preset flow feed rate range, then the feed rate of nutrient solution flow is sent to the feeding operation subunit. If the feed rate of nutrient solution flow is not within the preset flow feed rate range, then the preset target feed rate of nutrient solution flow is sent to the feeding operation subunit.

As shown in the aforesaid embodiments, the method and device of the invention comprise collecting samples of biological cells from the fermenting tank and obtaining current status information of biological cells based on the samples, comparing current status information of biological cells with preset target status information to obtain a difference between current status information of biological cells and target status information, controlling a feed rate of nutrient solution flow to a fermenting tank based on the obtained difference status. In this way, the biological fermentation process can be controlled based on the status information of the biological cells during the fermentation process to thereby improve the consistency during the fermentation process.

In addition, the method and device do not require complicated data analysis and can achieve real-time control of the biological fermentation process through a closed feedback loop. Moreover, the method and device do not induce control delay, while advantageously achieving automatic control of cell status during the fermentation process.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

Exemplary embodiments of the invention are explained in more detail below with reference to a drawings, in which.

DETAILED DESCRIPTION OF THE PREFERRED EMBODIMENTS

The method provided by the present invention mainly comprises collecting biological cell samples from a fermenting tank and obtaining current status information of biological cells according to the collected biological cell samples, comparing the current status information of biological cells with preset target status information to obtain a difference status between the current status information of biological cells and the target status information, and controlling the feed rate of nutrient solution flow to the fermenting tank based on the obtained difference status.

Figure 1:
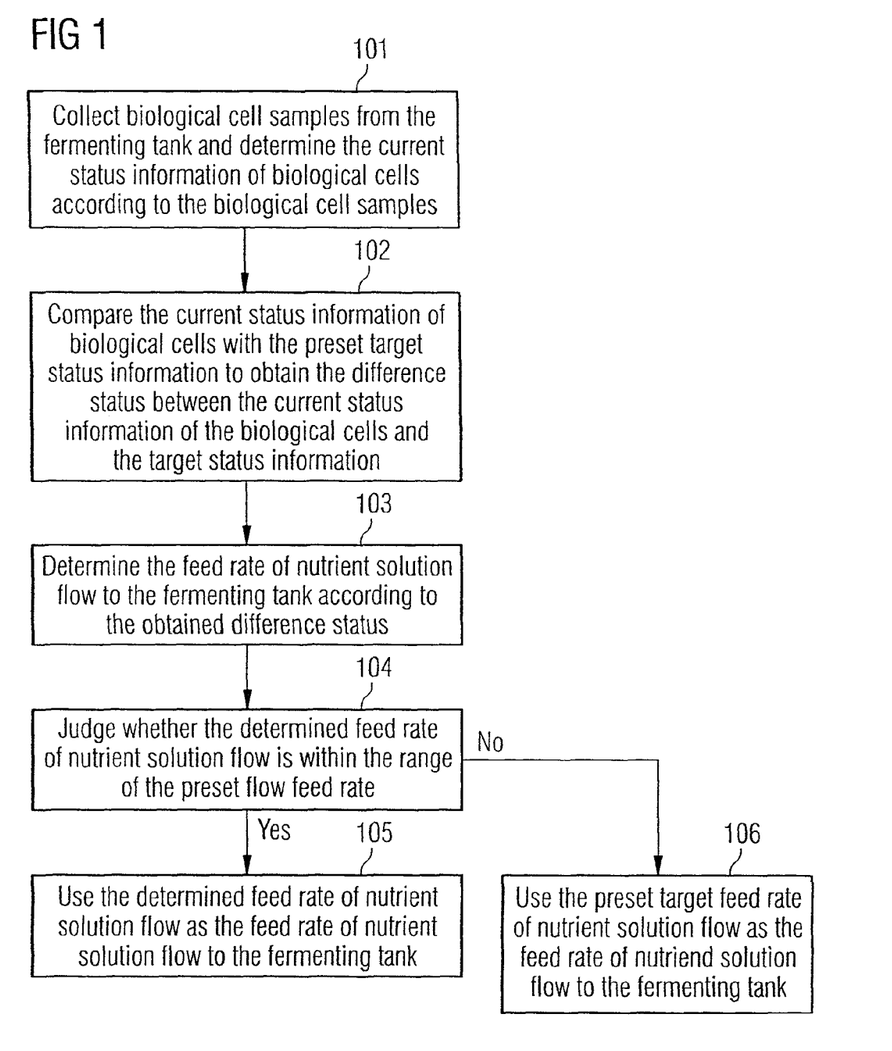
FIG. 1 is a flow chart of the method in accordance with an embodiment of the invention.

This method is described in detail by referring to a particular embodiment below. FIG. 1 is a flow chart of the method in accordance with an embodiment of the present invention. As shown in FIG. 1, the method may comprise collecting biological cell samples from the fermenting tank and obtaining the current status information of the biological cells based on the collected biological cell samples, as indicated in step 101.

Figure 2:
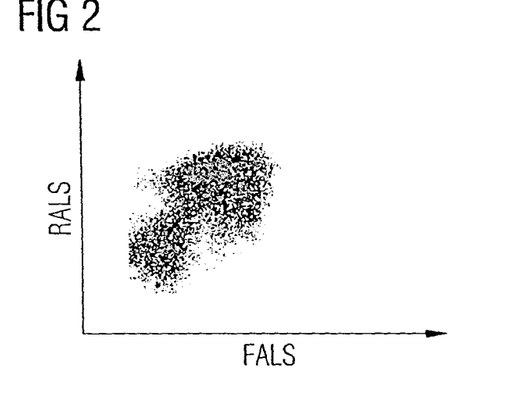
FIG. 2 is a current FALS-RALS graphical scatter plot of biological cells provided by the embodiments of the invention.

Here, real-time collection of biological cell samples and determination of status information of biological cells can be achieved by using a biological cell status determination instrument, such as a flow cytometer (FCM). The FCM injects the collected biological cell samples into the center of a sheath fluid, and causes the biological cells to align in a single line and form a cell bundle under the restriction of sheath fluid. After being excited by laser, the cell bundle produces a scattering light, of which the forward angle light scattering (FALS) and right angle light scattering (RALS) are collected and undergo photoelectric signal conversion. The electrical pulse signals obtained from FALS and RALS undergoing photoelectric signal conversion form a FALS-RALS scatter plot, from which cell concentration information, cell size information and cell form information can be obtained. The FALS-RALS scatter plot may be as shown in FIG. 2, where the x axis indicates the electrical FALS pulse signals and the y axis indicates the electrical RALS pulse signals. In addition, cells may also be first dyed with a fluorescent dye, where the waveband of the scattered light produced by the laser-excited cell bundle is detected, and the obtained waveband information is used to form a scatter plot of waveband information, from which cell structure information and cell metabolism information can be obtained. In this way, the present invention is not limited to the method for acquiring specific cell status information.

Next, the current status information of biological cells is compared with the preset target status information to obtain a difference status between the current status information of biological cells and the preset target status information, as indicated in step 102.

If a FALS-RALS scatter plot is obtained from FCM, the preset target status information may be the optimal FALS-RALS scatter plot obtained from previous fermentation batches, or may be the optimal FALS-RALS scatter plot obtained from experiments. The optimal FALS-RALS scatter plot may be the FALS-RALS scatter plot that reflects the highest cell concentration and the best product expression rate.

Figure 3:
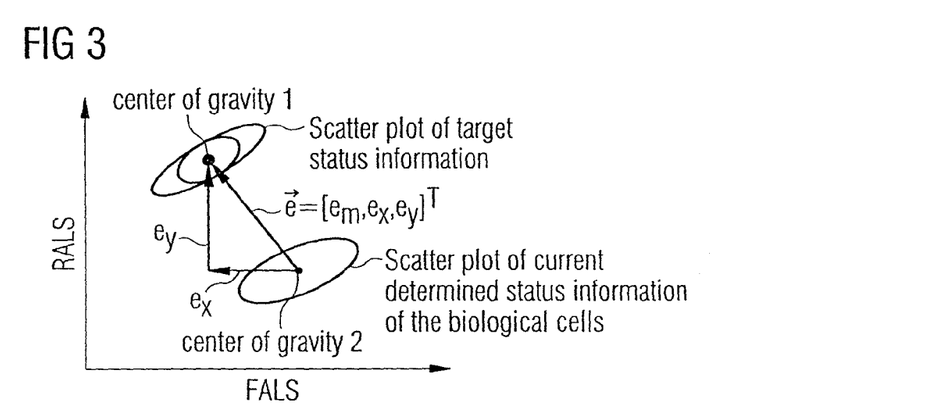
FIG. 3 is a schematic diagram showing acquisition of status difference information of biological cells provided by the embodiments of the present invention.

The difference status between the current status information of biological cells and the target status information may be expressed by a vector $\vec{e}$. Taking the FALS-RALS scatter plot as an example, FIG. 3 is a schematic diagram showing the steps for obtaining the vector, $\vec{e}$, where the scatter plot of target status information and the scatter plot of current status information of biological cells are displayed in the same FALS-RALS coordinate system. The center of gravity of the scatter plot for target status information is determined as the center of gravity 1. The center of gravity of the scatter plot for current status information of biological cells is determined as the center of gravity 2. The vector $\vec{e}$ starts from the center of gravity of the scatter plot for current status information of biological cells, and points to and ends at the center of gravity of the scatter plot for target status information, i.e., vector $\vec{e}$ starts from the center of gravity 2 and points to and ends at the center of gravity 1. The vector $\vec{e}$ can be expressed in accordance with the relationship:

$$\vec{e}=[e_m,e_x,e_y]^\tau.$$

Here, $e_m$ indicates a density difference between the scatter plot for current status information of biological cells and the scatter plot for target status information, characterizing the difference between cell concentration during current fermentation process and target cell concentration; $e_x$ indicates the difference between the center of gravity 2 and the center of gravity 1, characterizing the difference in size between the cells, during the current fermentation process and the target cell size; $e_y$ indicates the difference between the center of gravity 1 and the center of gravity 2 in the y axis, characterizing the difference in form between the cell form during current fermentation process and the target cell form. Consequently, the vector $\vec{e}$ can be used to characterize the difference in cell concentration, cell size and cell form between the status information during current fermentation process and the target status information.

The feed rate of nutrient solution flow into the fermenting tank is determined based on the obtained difference status information, as indicated in step 103.

Here, the vector $\vec{e}$ may be first converted to a scalar according to the preset conversion strategy to utilize the difference status in a more straightforward and direct way. In certain embodiments, the conversion methodology is, a linear conversion or a non-linear conversion.

The converted scalar e may be expressed as $e=f(\vec{e})$, where f is the adopted conversion methodology. Here, taking linear conversion as the example, the converted scalar e may be expressed as:

$$e=[k_1,k_2,k_3]\vec{e}.$$

Here, $0 \le k_1,k_2,k_3 \le 1$. $k_1,k_2,k_3$ may indicate the weights of cell concentration, cell size and cell form in the control process respectively, and can be set according to specific control requirements. For example, if the only purpose of fermentation process control is to allow the cell concentration to approach as close as possible to the target cell concentration, then $k_2$ and $k_3$ may be set to 0 and $k_1$ may be set to 1.

After the scalar e is obtained from the conversion, the feed rate of nutrient solution flow to the fermenting tank is determined according to the scalar e. The determination process is conducted based on the predetermined flow feed rate determination methodology so that the determined feed rate of nutrient solution flow can minimize the difference between the status information of biological cells during fermentation process and the target status, i.e., the status information of biological cells in the fermenting tank converges to the target status information. The specific flow feed rate determination methodologies can be in various forms, e.g., proportional-integral-derivative (PID), model predictive control, fuzzy control and neural network control. Here, taking the PID methodology as the example, the feed rate F(t) of nutrient solution flow to the fermenting tank may be expressed in:

$$F(t)=F_p(t)+K_c\left[e(t)+\frac{1}{\tau_i}\int_0^t e(t)dt+\tau_D\frac{de(t)}{dt}\right]$$

Here, $F_p(t)$ indicates the preset target feed rate of nutrient solution, and proportionality constant $K_c$ and integration constant $\tau_1$ may be determined by experimental paradigms according to the dynamic response of biological cells in the fermenting tank. For example, $K_c$ and $\tau_1$ that minimize the scalar e may be determined by the dynamic response information of biological cells in the fermenting tank during experiments. The measured noise of the biological attribute is large. Accordingly, integration may be neglected, i.e., $\tau_D$ may be set to 0 and the constants in F(t) should be selected in a way to minimize the scalar e.

The feed rate of nutrient solution flow determined at this point may be used as the feed rate of nutrient solution flow to the fermenting tank and the process is now finished. In preferred embodiments, the additional step of judging whether the determined feed rate of nutrient solution flow is within the preset range of feed rate may be performed, as indicated in step 104. If yes, then proceed to step 105. If no, then proceed to step 106.

Figure 4:
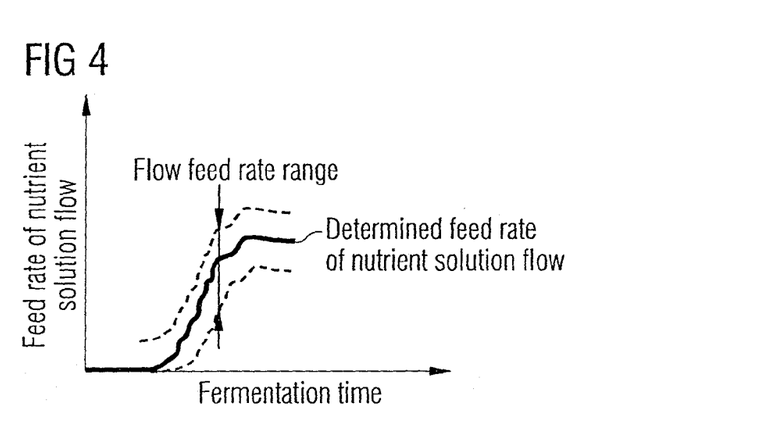
FIG. 4 is a schematic diagram showing that the determined feed rate of nutrient solution flow is within the preset range of flow feed rate provided by the embodiments in accordance with the invention.

As various noises or device failures in the control device may cause considerable error in the determined nutrient feed rate, the flow feed rate range can be preset to prevent such considerable error from affecting the fermentation process control. The flow feed rate range is the acceptable range of feed rates of nutrient solution flow. If the determined feed rate of nutrient solution flow is within the flow feed rate range, as shown in FIG. 4, it indicates that there is no considerable error and the determined feed rate of nutrient solution flow can be directly used as the feed rate of nutrient solution flow to the fermenting tank. Conversely, if the determined feed rate of nutrient solution flow is outside the flow feed rate range, then it indicates that there is considerable error and the preset target feed rate of nutrient solution flow is directly used as the feed rate of nutrient solution flow to the fermenting tank, as shown in steps 105 and 106 below. If the determined feed rate is within the flow feed rate range, then the determined feed rate of nutrient solution flow is next used as the feed rate of nutrient solution flow to the fermenting tank and the process is then ended, as indicated in step 105.

If the determined feed rate is outside the flow feed rate range, then the preset target feed rate of nutrient solution flow is used as the feed rate of nutrient solution flow to the fermenting tank and the process is ended, as indicated in step 106.

Various steps in the aforesaid process occur during the fermentation process, and step 101 is re-executed following step 106. Consequently, a closed-loop feedback control process is formed.

Figure 5:
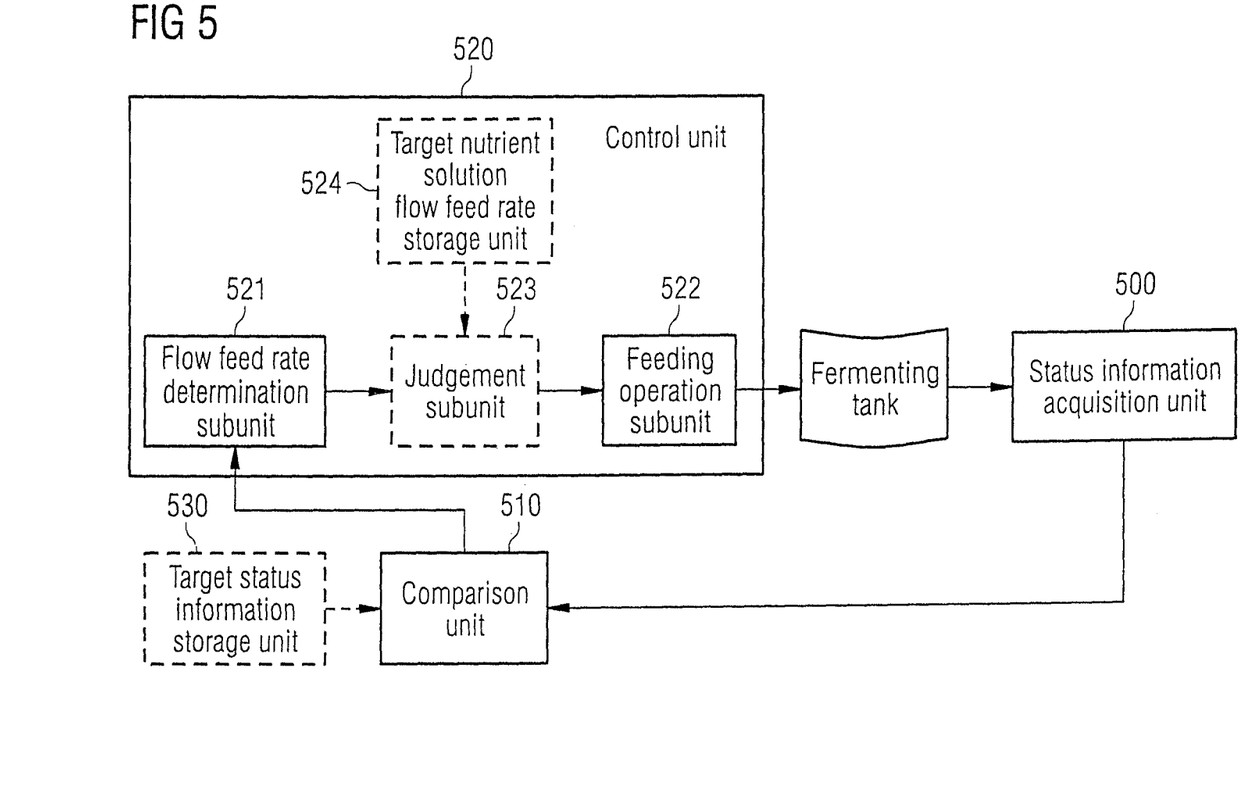
FIG. 5 shows a schematic block diagram of the structure of the device in accordance with an embodiment of the invention.

The above is the detailed description of the disclosed embodiments of the method in accordance with the present invention, and the device of the present invention is described below. FIG. 5 shows a schematic block diagram of the structure of a device in accordance with an embodiment of the present invention. As shown in FIG. 5, the device may comprise a status information acquisition unit 500, a comparison unit 510 and a control unit 520.

The status information acquisition unit 500 is used to collect samples of biological cells from a fermenting tank and obtain the status information of the current biological cells according to the collected biological cell samples.

The comparison unit 510 is used to compare the current status information of the biological cells with preset target status information, obtain the difference status between the current status information of the biological cells and preset target status information, and to provide the difference status to the control unit 520.

The control unit 520 is used to control the feed rate of nutrient solution flow into the fermenting tank based on the difference status.

Figure 6:
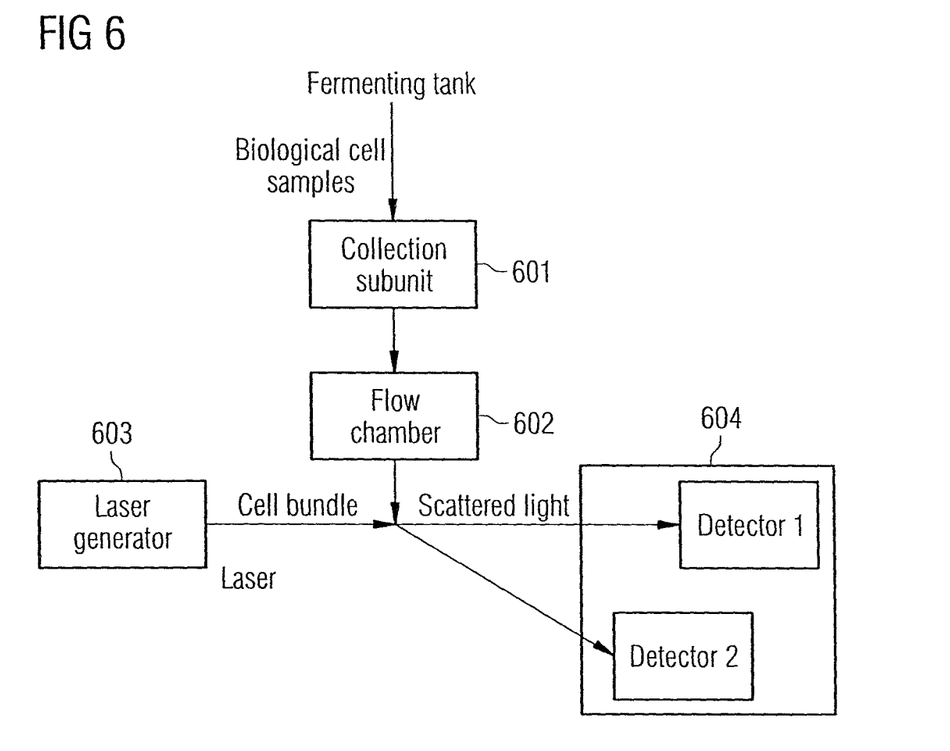
FIG. 6 is a schematic block diagram showing the structure of a flow cytometer in accordance with an embodiment of the invention.

Here, the status information acquisition unit 500 may comprise a flow cytometer and the specific structure is shown in FIG. 6. The flow cytometer may comprise a collection subunit 601, a flow chamber 602, a laser generator 603 and a detector 604.

The collection subunit the 601 is used to collect samples of biological cells from fermenting tank and inject the collected samples into the center of sheath fluid in the flow chamber 602.

The flow chamber 602 is used to allow biological cells in the collected samples to align in a single file and form a cell bundle under restriction of the sheath fluid.

The laser generator 603 is used to generate a laser and excite the cell bundle to produce light information.

The detector 604 is used to obtain the current status information of biological cells from the light information.

The detector 604 may be a photodiode or a photomultiplier tube, which collects scattered light or fluorescence produced by laser-excited cells and converts light into electrical signals. The converted electrical signals can be used to form the status information scatter plot. For example, FALS and RALS scattered light can be collected and converted to obtain a FALS-RALS scatter plot and scattered light may be detected for a waveband to obtain a waveband information scatter plot; cell concentration information, cell size information and cell form information can be obtained from the FALS-RALS scatter plot, and cell structure information and cell metabolism information can be obtained from waveband information scatter plot. The detector 1 in detector 604 shown in FIG. 6 can collect FALS scattered light and convert light into electrical signals, and detector 2 can collect RALS scattered light and convert light into electrical signals.

The comparison unit 510 can implement the method in accordance with step 102 depicted in FIG. 1 to conduct comparisons and obtain the difference status. With the FALS-RALS scatter plot as an example, the comparison unit 510 can firstly determine the center of gravity of the scatter plot for target status information, expressed as center of gravity 1, and the center of gravity of the scatter plot for current status information of biological cells, expressed as center of gravity 2, and take the vector $\vec{e}$ starting from the center of gravity 2 and pointing to and ending at the center of gravity 1 to indicate the difference between the current status information of biological cells and target status information, and then provide the vector $\vec{e}$ to the control unit 520. The control unit 520 can firstly convert the vector $\vec{e}$ to a scalar according to a predetermined conversion methodology, and then take the converted scalar e as a variable to determine the nutrient feed rate according to a predetermined flow feed rate determination methodology that allows the status information of biological cells in the fermenting tank to converge to the target status information, where, the feed rate determination strategy includes various modes, such as a PID methodology.

In an embodiment, the device also comprise a target status information storage unit 530 for storing target status information.

Here, the target status information storage unit 530 can store target status information that corresponds to different application needs, where an operator can select target status information suited to the current fermentation process according to different application needs for the comparison unit 510 to conduct comparisons, and can update target status information at any time as needed.

The comparison unit 510 is also used to obtain target status information from the target status information storage unit 530.

Here, the control unit 520 may comprise a flow feed rate determination subunit 521 and a feeding operation subunit 522.

The flow feed rate determination subunit 521 is used to determine the feed rate of nutrient solution flow according to the difference status by using the predetermined flow feed rate determination methodology that causes the status information of biological cells in the fermenting tank to converge to the target status information, and send the feed rate of nutrient solution flow to the feeding operation subunit 522.

The feeding operation subunit 522 is used to feed the nutrient solution flow to the fermenting tank based on the received feed rate of nutrient solution flow.

In alternative embodiments, the control unit 520 also comprises a judgment subunit 523, which is used to receive the feed rate of nutrient solution flow from the flow feed rate determination subunit 521, and judge whether the feed rate of nutrient solution flow is within the preset range of flow feed rate. If the feed rate of nutrient solution flow is within the preset range of flow feed rate, then the feed rate of nutrient solution flow is sent to the feeding operation subunit 522. If the feed rate of nutrient solution flow is not within the preset range of flow feed rate, then the preset target feed rate of nutrient solution flow is sent to the feeding operation subunit 523.

In other embodiments, the control unit 520 also comprises a target nutrient solution flow feed rate storage unit 524, which is used to store the target feed rate of nutrient solution flow and the flow feed rate range, and the judgment subunit 523 can obtain the target feed rate of nutrient solution flow and flow feed rate range from the target nutrient solution flow feed rate storage unit 524.

Here, the target nutrient solution flow feed rate storage unit 524 can store the target feed rate of nutrient solution flow and the flow feed rate range that correspond to different application needs, and an operator can select a target nutrient feed rate and feed rate range suited to the current fermentation process based on different applications needs for judgment subunit 523 to conduct judgment, and can update the target nutrient feed rate and feed rate range at any time as needed.

As shown in the above, the method and device in accordance with the disclosed embodiments of the present invention comprise collecting biological cell samples from the fermenting tank and obtaining the current status information of biological cells based on the collected biological cell samples, comparing the current status information of biological cells with the preset target status information to obtain a difference status between the current status information of biological cells and the target status information, controlling the feed rate of nutrient solution flow to the fermenting tank the obtained difference status. In this way, the biological fermentation process can be controlled based on the status information of the biological cells during fermentation, and the consistency of the fermentation process and product quality can be improved.

Moreover, the method and device of the disclosed embodiments of the invention do not require complicated data analysis and can achieve real-time control of the biological fermentation process by using a closed feedback loop. The automatic control of cell status during the fermentation process is achieved without any control delay.

Preferably, the method and device in accordance with the disclosed embodiments can make further judgements about the feed rate of nutrient solution flow that is determined based on the difference information, i.e., judge whether the determined feed rate of nutrient solution flow is within the preset feed rate range. If the determined feed rate of nutrient solution flow is within the preset feed rate range, the determined feed rate of nutrient solution flow is used for feeding the nutrient solution to the fermenting tank. If the determined feed rate of nutrient solution flow is not within the preset feed rate range, then the preset target feed rate of nutrient solution flow is used for feeding the nutrient solution to the fermenting tank. As a result, the feed rate of nutrient solution flow to the fermenting tank can be maintained in an acceptable range to prevent the definite errors caused by various noises or device failures of the control device.

The above only describes the preferred embodiments according to the present invention, and is not intended to limit the protective scope of the present invention. Any modifications, equivalent substitutions and improvements within the spirit and principle of the invention should fall within the protective scope of the present invention.

Thus, while there are shown, described and pointed out fundamental novel features of the invention as applied to preferred embodiments thereof, it will be understood that various omissions and substitutions and changes in the form and details of the illustrated apparatus, and in its operation, may be made by those skilled in the art without departing from the spirit of the invention. Moreover, it should be recognized that structures shown and/or described in connection with any disclosed form or embodiment of the invention may be incorporated in any other disclosed or described or suggested form or embodiment as a general matter of design choice.

The invention claimed is:

1. A device for controlling a fermentation process, comprising:
 a status information acquisition unit configured to collect biological cell samples of biological cells from a fermenting tank and to obtain current status information of the biological cells based on the collected biological cell samples;
 a control unit configured to control a feed rate of nutrient solution flow to said fermenting tank according to a difference status between the current status information of the biological cells and the preset target status information; and
 a comparison unit configured to compare said current status information of the biological cells with a preset target status information, obtain the difference status between the current status information of the biological cells and the preset target status information, and to provide the difference status to said control unit.

2. The device as claimed in claim 1, wherein said status information acquisition unit is a flow cytometer comprising:
 a collection subunit configured to collect the biological cell samples from the fermenting tank and inject the collected biological cell samples into a center of sheath fluid in a flow chamber configured to allow collected biological cell samples to align in a single line and form a cell bundle under restriction of the sheath fluid;
 a laser generator configured to generate a laser and excite said cell bundle to produce light information; and a detector configured to obtain the current status information of the biological cells from said light information.

3. The device as claimed in claim 1, wherein the device further comprises:
a target status information storage unit for storing the target status information, the comparison unit being further configured to obtain said target status information from said target status information storage unit.

4. The device as claimed in claim 1, wherein said control unit comprises:
a feeding operation subunit configured to feed the nutrient solution to said fermenting tank based on the determined feed rate of nutrient solution flow;
a flow feed rate determination subunit configured to determine the feed rate of nutrient solution flow based on said difference status by using a preset flow feed rate determination methodology which causes the current status information of the biological cells in said fermenting tank to converge to said preset target status information, and to send the determined feed rate of nutrient solution flow to said feeding operation subunit.

5. The device as claimed in claim 4, wherein said control unit further comprises:
a judgment subunit configured to receive the determined feed rate of nutrient solution flow sent from said flow feed rate determination subunit, and to judge whether the determined feed rate of nutrient solution flow is within a preset flow feed rate range;
wherein the judgment subunit sends the determined feed rate of nutrient solution flow to said feeding operation subunit if the feed rate of nutrient solution flow is within a preset flow feed rate range and sends a preset target flow feed rate of nutrient solution flow to said feeding operation subunit if the feed rate of nutrient solution flow is not within the preset flow feed rate range.

* * * * *